US006093517A

United States Patent [19]
Ito et al.

[11] Patent Number: 6,093,517
[45] Date of Patent: Jul. 25, 2000

[54] CALIXARENES FOR USE AS DISSOLUTION INHIBITORS IN LITHOGRAPHIC PHOTORESIST COMPOSITIONS

[75] Inventors: Hiroshi Ito, San Jose, Calif.; Tomonari Nakayama, Yamagata; Mitsuru Ueda, Tori-machi, both of Japan

[73] Assignee: International Business Machines Corporation, Armonk, N.Y.

[21] Appl. No.: 09/127,325

[22] Filed: Jul. 31, 1998

[51] Int. Cl.$^7$ .............................. G03F 7/039; C07C 41/00
[52] U.S. Cl. ...................... 430/270.1; 568/633; 568/632; 568/640; 568/719; 562/466
[58] Field of Search ......................... 430/270.1; 562/466; 568/633, 632, 640, 719

[56] References Cited

U.S. PATENT DOCUMENTS

| | | | |
|---|---|---|---|
| 4,491,628 | 1/1985 | Ito et al. | 430/176 |
| 5,580,694 | 12/1996 | Allen et al. | 430/270.1 |
| 5,625,020 | 4/1997 | Breyta et al. | 526/329.2 |
| 5,688,998 | 11/1997 | Ichimura et al. | 562/466 |

OTHER PUBLICATIONS

Sakamizu, T. et al, J.Photopoly.Sci.Technol., 11(4), 1998, 547–552.
Hayashi, Y., J.Chem.Soc.Perkin Trans.2, 2(4), Apr. 1998, 981–987.
Abis, L. et al, J.Org.Chem., 53, 1988, 5475–5479.
Botta, B. et al, J.Org.Chem., 59, 1994, 1532–1541.
Chemical Abstracts 117:234117 of Mendeleev Commun., 3, 1992, 106–8. pp. 14–16 provided of Chemical Abstracts computer printout of the abstract.
Allen et al. (1995), "Resolution and Etch Resistance of a Family of 193 nm Positive Resists," *J. Photopolm. Sci. and Tech.* 8(4):623–636.
Arduini et al. (1984), "ρ–t–Butyl–Calix[4]arene Tetracarboxylic Acid. A Water Soluble Calixarene in a Cone Structure," *J. Chem. Soc., Chem. Commun.*:981–982.
Fujita et al. (1996), "Ultrahigh Resolution of Calixarene Negative Resist in Electron Beam Lithography," *Appl. Phys. Lett.* 68(9):1297–1299.
Gutsche (1983), "Calixarenes," *Acc. Chem. Res.* 16:161–170.
Ito et al. (1994), "Environmentally Stable Chemical Amplification Positive Resist: Principle, Chemistry, Contamination Resistance, and Lithographic Feasibility," *J. Photopolym. Sci. and Tech.* 7(3):433–448.
Nakayama et al. (1997), "A Negative–Working Alkaline Developable Photoresist Based on Calix[4]resourcinarene, a Cross–linker, and a Photoacid Generator," *Chem. Lett.*:265–266.
Ohnishi et al. (1997), "Calixarene Resists for Nano–Lithography," *Proc. ACS Div. Polym. Mater. Sci. Eng.* 77:453–454.
Ueda et al. (1997), "A Negative–Working Alkaline Developable Photoresist Based on Calix[4]resocinarenes, a Cross–linker, and a Photoacid Generator," *Proc. ACS Div. Polym. Mater. Sci. Eng.* 77:455–456.

*Primary Examiner*—Janet Baxter
*Assistant Examiner*—Rosemary Ashton
*Attorney, Agent, or Firm*—Dianne E. Reed; Reed & Associates

[57] ABSTRACT

A lithographic photoresist composition is provided containing novel calixarene compounds, particularly calix[4] resorcinarenes that are partially or wholly protected with acid-labile functionalities, as dissolution inhibitors. Also provided is a process for using the composition to generate resist images on a substrate is provided, i.e., in the manufacture of integrated circuits or the like.

52 Claims, 4 Drawing Sheets

CALIXARENES FOR USE AS DISSOLUTION INHIBITORS IN LITHOGRAPHIC PHOTORESIST COMPOSITIONS

TECHNICAL FIELD

This invention relates generally to photolithography, and more particularly pertains to dissolution inhibitors for use in a lithographic photoresist composition. The invention additionally pertains to novel compounds useful as dissolution inhibitors, to novel photoresist compositions containing the dissolution inhibitors, and to methods for using the photoresist composition to generate a resist image on a substrate.

BACKGROUND

Lithography involving shorter-wavelength, "deep" ultraviolet ("DUV") radiation (less than 300 nm), as well as lithographic processes involving electron-beam (e-beam) and x-ray exposure techniques, have become indispensable to the microelectronics industry. Improvement of these systems continues to be of the utmost importance.

In use, a radiation-sensitive lithographic photoresist composition is applied as a thin coating on a substrate (i.e., a wafer), and the coated substrate is subsequently "baked" to remove the casting solvent. The photoresist film is then exposed to radiation in an imagewise fashion (through a mask, with DUV and x-ray lithography, or directly, with e-beam lithography), and the image is then developed, typically by immersion in a developer solvent. With a positive resist composition, the developer removes exposed areas of the composition while leaving unexposed areas intact. With a negative resist composition, the developer removes unexposed areas of the composition while leaving exposed areas intact. Thus, for the process to be effective, there must be a differential between the solubility of the exposed photoresist and the solubility of the unexposed photoresist in the developer solvent. Indeed, one of the ways in which the industry has attempted to improve lithographic photoresist compositions has been to modify such compositions, in one fashion or another, with regard to solubility characteristics.

For example, U.S. Pat. No. 4,491,628 to Ito et al., assigned to IBM Corporation, describes deep UV photoresist compositions containing a polymer bearing acid-labile pendant groups, e.g., t-butyl esters of carboxylic acids, t-butyl carbonates of phenols, and the like. The solubility characteristics of the polymers change markedly upon acidolysis, i.e., upon acid cleavage of the pendant groups. When the resist is imagewise exposed to radiation, the photoinitiator contained in the exposed portions of the resist generates an acid, and the polymer undergoes cleavage. In the unexposed portions of the resist, the polymer remains intact. The intact polymer in the unexposed portions of the resist is soluble in a nonpolar solvent but insoluble in an alkaline or polar solvent, while the acid-cleaved polymeric product in the exposed portions of the resist is, by contrast, insoluble in a nonpolar solvent but soluble in an alkaline or polar solvent. The differential in solubility between the intact polymer and the acid-cleaved polymeric product serves as the basis for developing the image, and can be used to enable image reversal depending on the polarity of the solvent used to develop the image.

Following this initial work with homopolymers, lithographic photoresist compositions were next prepared using copolymers, e.g., copolymers formed from acrylate, methacrylate and/or styrene monomers, and a technique known as "chemical amplification." With chemical amplification, a single photochemical event essentially triggers a cascade of subsequent chemical transformations, resulting from the catalytic activity of the initially generated species. A particular copolymer of interest is described by Ito et al. (1994), in "Environmentally Stable Chemical Amplification Positive Resist: Principle, Chemistry, Contamination Resistance and Lithographic Feasibility," *J. Photopolym. Sci. and Tech.* 7(3):433–448, which pertains to a positive resist composition designated as an "Environmentally Stable Chemical Amplification Positive Resist" or an "ESCAP." The polymer in the disclosed resist composition is a copolymer of 4-hydroxystyrene and t-butyl acrylate. As in the '628 patent discussed above, the copolymer of the resist composition undergoes marked changes in solubility characteristics upon removal of acid-labile protecting groups.

U.S. Pat. No. 5,625,020 to Breyta et al., assigned to IBM Corporation, also describes a chemically amplified photosensitive resist composition. As in Ito et al. (1994), this patent emphasizes the use of a copolymer in the resist composition, which, depending on the presence or absence of certain pendant groups, is either soluble or insoluble in the selected developer. The disclosed polymers are copolymers of hydroxystyrene and either acrylate monomers, methacrylate monomers, or a mixture of acrylate and methacrylate monomers.

The use of dissolution inhibitors in lithographic photoresist compositions has also been proposed, and, indeed, acid-sensitive dissolution inhibitors are often incorporated into current, commercially available photoresists. With positive resists, the dissolution inhibitors are compounds that inhibit dissolution of the resist under basic conditions but allow and in fact facilitate dissolution under acidic conditions, i.e., after exposure to radiation.

Dissolution inhibitors that have been used, to date, include lower alkyl esters of cholic, ursocholic and lithocholic acid, including methyl cholate, methyl lithocholate, methyl ursocholate, t-butyl cholate, t-butyl lithocholate, t-butyl ursocholate, and the like (see, e.g., Allen et al. (1995), "Resolution and Etch Resistance of a Family of 193 nm Positive Resists," *J. Photopolym. Sci. and Tech.* 8(4):623–636); hydroxyl-substituted analogs of such compounds (ibid.); and androstane-17-alkylcarboxylates substituted with 1 to 3 $C_1$–$C_4$ fluoroalkyl carbonyloxy substituents, such as t-butyl trifluoroacetyllithocholate (see, e.g., U.S. Pat. No. 5,580,694 to Allen et al.). Still other acid-labile dissolution inhibitors are shown below:

-continued

"BisBOC":

The currently available dissolution inhibitors are, however, relatively weak in their dissolution inhibition effects and do not provide optimum developer selectivity or development contrast. The present invention is directed to a new class of dissolution inhibitors which overcome the aforementioned disadvantages in the art. The dissolution inhibitors now provided are in the calixarene family, and, more particularly, are calix[4]resorcinarenes that are partially or wholly protected, preferably with acid-labile functionalities.

Calixarenes were discovered and methods of synthesis devised therefor in the 1950's. See, for example, Hayes et al. (1956) *Chem. Ind. (Berlin)*, at p. 193 and Hayes et al. (1958) *J. Appl. Chem.* 8:743. Initial work with these compounds focused on potential biological applications, particularly in constructing systems for mimicking the catalytic activity of certain enzymes. Gutsche (1983), "Calixarenes," *Acc. Chem. Res.* 16:161–170. Other work has suggested utility as synthetic analogues of cyclodextrins, and in extraction and separation processes. Arduini et al. (1984), "p-t-Butyl-Calix[4]arene Tetracarboxylic Acid. A Water Soluble Calixarene in a Cone Structure," *J. Chem. Soc., Chem. Commun.*, at pp. 981–982. The only references pertaining to potential use of calixarene-type compounds in lithography are Fujita et al. (1996), "Ultrahigh Resolution of Calixarene Negative Resist in Electron Beam Lithography," *Appl. Phys. Lett.* 68(9):1297–1299, Ohnishi et al. (1997), "Calixarene Resists for Nano-Lithography," *Proc. ACS Div. Polym. Mater. Sci. Eng.* 77: 453–454, Nakayama et al. (1997), "A Negative-Working Alkaline Developable Photoresist Based on Calix[4]resorcinarene, a Cross-linker, and a Photoacid Generator," *Chem. Lett.*, at pp. 265–266, and Ueda et al. (1997), "A Negative-Working Alkaline Developable Photoresist Based on Calix[4]resorcinarenes, a Crosslinker, and a Photoacid Generator," *Proc. ACS Div. Polym. Mater. Sci. Eng.* 77: 455–456. However, each of these publications describes cross-linked calixarenes as the polymeric component of the photoresist, and fails to recognize the potential utility of a calixarene compound as a dissolution inhibitor. Furthermore, none of these references suggest that calixarenes which are partially or wholly protected, either with acid-labile protecting groups or other moieties, could be desirable for any purpose.

Accordingly, the present invention is directed to the discovery that certain compounds in the calixarene family are excellent dissolution inhibitors in a lithographic photoresist composition. The invention represents an important advance in the art, insofar as developer selectivity is greatly increased and substantially higher dissolution inhibition is provided. These features in turn give rise to high development contrast and utility at relatively low concentrations. The compounds can also be used in conjunction with a variety of polymers, resist components, and customary optional additives, as will be discussed in detail herein. As noted above, the present dissolution inhibitors are in the calixarene family, and, more particularly, are calix[4]resorcinarenes that are partially or wholly protected, preferably with acid-labile functionalities. That is, calix[4]resorcinarenes are cyclic tetramers of resorcinol and possess eight phenolic OH groups, and in the compounds of the invention at least one of the phenolic OH groups is protected, preferably with an acid-labile protecting group to give an acid-labile dissolution inhibitor. Photochemically induced acid-catalyzed deprotection regenerates the unprotected calix[4]resorcinarene, which dissolves extremely rapidly in aqueous base.

SUMMARY OF THE INVENTION

It is a primary object of the invention to address the above-described need in the art by providing a lithographic photoresist composition containing, as a dissolution inhibitor, a calix[4]resorcinarene that is partially or wholly protected with a protecting group.

It is another object of the invention to provide such a composition wherein the calix[4]resorcinarene is partially or wholly protected with an acid-labile protecting group.

It is an additional object of the invention to provide such a composition containing, in addition to the calix[4]resorcinarene dissolution inhibitor, both a radiation-sensitive acid generator and a polymer.

It is still another object of the invention to provide such a composition in which the polymer undergoes a change in solubility characteristics in the presence of acid.

It is a further object of the invention to provide such a composition in which the polymer bears acid-labile functionalities.

It is still a further object of the invention to provide such a composition in which the polymer is acid-stable.

It is another object of the invention to provide a method for generating a resist image on a substrate using a photoresist composition as described herein.

It is a further object of the invention to provide novel compounds comprising calix[4]resorcinarenes that are partially or wholly protected.

It is yet a further object of the invention to provide novel compounds comprising calix[4]resorcinarenes that are partially or wholly protected with acid-labile protecting groups.

Additional objects, advantages and novel features of the invention will be set forth in part in the description which follows, and in part will become apparent to those skilled in the art upon examination of the following, or may be learned by practice of the invention.

In one embodiment, then, the present invention relates to a lithographic photoresist composition comprising a calix [4]resorcinarene compound as a dissolution inhibitor, wherein the calix[4]resorcinarene is partially or wholly protected with protecting groups (designated R in formula (I)). Preferred such compounds have the structure of formula (I)

wherein:

the R moieties are independently selected from the group consisting of hydrogen, acid-labile protecting groups, and acid-inert protecting groups, with the proviso that at least one R is a protecting group;

the R' moieties are independently selected from the group consisting of hydrogen, halogen, nitro, alkyl, aryl, and alkaryl, and, if alkyl, aryl or alkaryl, optionally substituted with one to four substituents selected from the group consisting of hydroxy, halogen, lower alkyl, lower alkoxy and nitro; and the X and Y moieties may be the same or different and are selected from the group consisting of hydrogen, alkyl, alkenyl, alkynyl, alkoxy, aryl, aralkyl, alkaryl, halo, cyano, nitro and carboxylate.

Partially or wholly protected calix[4]resorcinarenes, including, but not limited to, those compounds encompassed by structure (I), are believed to be novel compounds and are claimed as such herein.

In a further embodiment, the present invention relates to the use of the novel resist composition to make integrated circuits. One such process involves the steps of (a) coating a substrate with a film comprising the aforementioned lithographic resist composition, containing a partially or wholly protected calix[4]resorcinarene as a dissolution inhibitor; (b) exposing the film selectively to a predetermined pattern of radiation to form a latent image therein; and (c) developing the image using a suitable developer composition. Step (b) involves the use of x-ray, electron beam or ultraviolet radiation, preferably "deep" ultraviolet radiation having a wavelength of less than about 300 nm, more preferably having a wavelength of 248 nm. In manufacturing processes wherein the contrast is typically not all that high, e.g., using a phase shift mask or x-ray processing, the novel dissolution inhibitors compensate and provide a marked improvement in contrast.

DETAILED DESCRIPTION OF THE INVENTION

Overview and Definitions:

Before describing the present invention in detail, it is to be understood that this invention is not limited to specific compositions, components or process steps, as such may vary. It is also to be understood that the terminology used herein is for the purpose of describing particular embodiments only, and is not intended to be limiting.

It must be noted that, as used in this specification and the appended claims, the singular forms "a," "and," and "the" include plural referents unless the context clearly dictates otherwise. Thus, for example, reference to "a calix[4] resorcinarene having the structure (I)" includes a combination of two or more compounds encompassed by structure (I), a "photosensitive acid generator" includes a mixture of two or more such compounds, and the like.

In describing and claiming the present invention, the following terminology will be used in accordance with the definitions set out below.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms, and the term "lower alkyl ester" refers to an ester functionality —C(O)O—R wherein R is lower alkyl.

The term "alkenyl" as used herein refers to a branched or unbranched hydrocarbon group of 2 to 24 carbon atoms containing at least one double bond, typically containing one to six double bonds, more typically one or two double bonds, e.g., ethenyl, n-propenyl, n-butenyl, octenyl, decenyl, and the like, as well as cycloalkenyl groups such as cyclopentenyl, cyclohexenyl and the like. The term "lower alkenyl" intends an alkenyl group of two to six carbon atoms, preferably two to four carbon atoms.

The term "alkynyl" as used herein refers to a branched or unbranched hydrocarbon group of 2 to 24 carbon atoms containing at least one triple bond, e.g., ethynyl, n-propynyl, n-butynyl, octynyl, decynyl, and the like, as well as cycloalkynyl groups such as cyclopentynyl, cyclohexynyl and the like. The term "lower alkynyl" intends an alkynyl group of two to six carbon atoms, preferably two to four carbon atoms.

The term "alkoxy" as used herein refers to a substituent —O—R wherein R is alkyl as defined above. The term "lower alkoxy" refers to such a group wherein R is lower alkyl.

The term "aryl" as used herein, and unless otherwise specified, refers to an aromatic moiety containing one to five aromatic rings. For aryl groups containing more than one aromatic ring, the rings may be fused or linked. Preferred monocyclic aromatic substituents are phenyl and substituted phenyl, optionally substituted with one to five, typically one to four, halo, alkyl, alkenyl, alkynyl, alkoxy, nitro or other substituents.

The term "halo" is used in its conventional sense to refer to a chloro, bromo, fluoro or iodo substituent. The terms "haloalkyl," "haloaryl" (or "halogenated alkyl" or "halogenated aryl") refers to an alkyl or aryl group, respectively, in which at least one of the hydrogen atoms in the group has been replaced with a halogen atom.

The term "alkaryl" refers to an aryl group with an alkyl substituent, wherein "aryl" and "alkyl" are as defined above.

The term "aralkyl" refers to an alkyl group that has an aryl substituent, wherein "alkyl" and "aryl" are as defined above.

The terms "photogenerated acid" and "photoacid" are used interchangeably herein to refer to the acid that is created upon exposure of the present compositions to radiation, i.e., as a result of the radiation-sensitive acid generator in the compositions.

The terms "acid-labile" or "acid-cleavable" are used interchangeably herein to refer to a molecular moiety that undergoes a change in structure upon contact with acid, e.g., an ester that, upon contact with acid, is hydrolyzed to an acid, a carbonate ester that, upon contact with acid, is hydrolyzed to a hydroxyl group, or the like. The groups that are "acid-labile" or "acid-cleavable" in the context of the present invention are also referred to as "acid-labile protecting groups" or simply as "acid-labile functionalities."

Conversely, the term "acid-inert" to refer to other protecting groups is intended to mean that a molecular moiety does not undergo a change in structure upon contact with acid, e.g., an alkoxy group or the like.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

For additional information concerning terms used in the field of lithography and lithographic compositions, reference may be had to *Introduction to Microlithography*, Eds. Thompson et al. (Washington, D.C.: American Chemical Society, 1994).

The present invention relates to the use of certain calixarenes as dissolution inhibitors in lithographic photoresist compositions. The calixarenes are calix[4]resorcinarenes that are partially or wholly protected with acid-labile protecting groups. That is, at least half of the free hydroxyl groups present on the calix[4]resorcinarene molecule are protected with protecting groups that are removable with acid.

Preferred calix[4]resorcinarenes have the structure of formula (I)

wherein the various substituents are defined as follows.

The R moieties are independently selected from the group consisting of hydrogen and acid-labile protecting groups, with the proviso that at least one, and preferably at least four, of the R moieties are acid-labile protecting groups. It will be appreciated that the symmetric location of the —OR moieties in the calix[4]resorcinarene of formula (I) corresponds to the positioning of the —OR moieties on the resorcinol starting material used to make these compounds. Suitable acid-labile protecting groups include, but are not limited to, moieties having the structure in which m is 0 or 1, n is 0 or 1, and $R^1$ is $CR^2R^3R^4$, $SiR^5R^6R^7$ or $GeR^5R^6R^7$ wherein $R^2$, $R^3$ and $R^4$ are independently hydrogen, alkyl, alkoxy, aryl, or aryloxy, typically hydrogen, lower alkyl or lower alkoxy, or are linked to form a cycloalkyl or cyclooxyalkyl ring, typically a five- or six-membered ring, and $R^5$, $R^6$ and $R^7$ are the same or different and are each an alkyl, typically a lower alkyl, substituent.

Thus, $R^1$ may be, for example, methoxymethyl, ethoxymethyl, methoxyethoxymethyl, benzyloxymethyl, cyclopropylmethyl, benzyl, diphenylmethyl, triphenylmethyl, 1-methoxyethyl, 1-methylethyl, 1,1-dimethoxyethyl, 1-ethoxyethyl, 1-ethylthioethyl, 1,1-diethoxyethyl, 1-phenoxyethyl, 1,1-diphenoxyethyl, 1-cyclopropylethyl, 1-phenylethyl, 1,1-diphenylethyl, isopropyl, s-butyl, t-butyl, 1,1-dimethylpropyl, 1-methylbutyl, 1,1-dimethylbutyl, trimethylsilyl, ethyldimethylsilyl, diethylmethylsilyl, triethylsilyl, dimethylisopropylsilyl, t-butyldimethylsilyl, di-t-butylmethylsilyl, tri-t-butylsilyl, dimethylphenylsilyl, methyldiphenylsilyl, triphenylsilyl, trimethylgermyl, ethyldimethylgermyl, diethylmethylgermyl, triethylgermyl, dimethylisopropylgermyl, methyldiisopropylgermyl, triisopropylgermyl, t-butyldimethylgermyl, di-t-butylmethylgermyl, tri-t-butylgermyl, dimethylphenylgermyl, methyldiphenylgermyl, triphenylgermyl, and the like. Other suitable acid-labile protecting groups may be found in U.S. Pat. No. 5,679,495 to Yamachika et al. or in the pertinent literature and texts (e.g., Greene et al., Protective Groups in Organic Synthesis, $2^{nd}$ Ed. (New York: John Wiley & Sons, 1991).

Representative —OR moieties:

The R' moieties are independently selected from the group consisting of hydrogen, halogen, nitro, alkyl, aryl, and alkaryl. When an R' is alkyl, aryl or alkaryl, it may be substituted with one to four substituents selected from the group consisting of hydroxy, halogen, lower alkyl, lower alkoxy and nitro. Examples of particularly preferred R' groups include, but are not limited to, hydrogen, bromo, $C_1$–$C_{12}$ alkyl, and $C_1$–$C_{12}$ alkyl substituted with a terminal hydroxyl group, a halogen atom, particularly bromo, a phenyl ring, or a phenyl ring bearing a hydroxy, halogen or lower alkyl substituent.

The X and Y moieties may be the same or different and are selected from the group consisting of hydrogen, alkyl, alkenyl, alkynyl, alkoxy, aryl, aralkyl, alkaryl, halo, cyano, nitro and carboxylate. In preferred compounds, the X moieties are all hydrogen, and the Y moieties are selected from the group consisting of hydrogen and lower alkyl.

It will be appreciated by those skilled in the art that the basic calix[4]resorcinarene molecule can exist in either of two isomeric forms, commonly referred to as the $C_{2V}$ and the $C_{4V}$ configurations (also sometimes referred to herein as the "ctt" and "ccc" isomers, respectively), as follows:

Calix[4]resorcinarene, the $C_{2V}$ Configuration ("ctt")

Calix[4]resorcinarene, the $C_{4V}$ Configuration ("ccc")

In the context of the invention, the protected and optionally substituted calix[4]resorcinarenes may be in either the $C_{2V}$ or the $C_{4V}$ configurations, or a combination of the two isomeric forms may be present.

The protecting moieties are introduced into the calix[4] resorcinarene molecule by reacting the unprotected calix[4] resorcinarene with a moiety which will then provide an acid-labile functionality on one or more of the eight hydroxyl groups. While at least one of the eight hydroxyl groups should be protected in this way, it is generally preferred that at least four of the eight hydroxyl groups be protected, and, most preferably, all eight hydroxyl groups are protected. The reaction may be conducted using conventional means, known to those skilled in the art. For example, to provide a calix[4]resorcinarene fully protected with the t-butoxycarbonylmethyl group, the unprotected calixresorcinarene may be reacted with eight equivalents of t-butyl bromoacetate and potassium carbonate. Similarly, to provide a calix[4]resorcinarene fully protected with the t-butoxycarbonyl (tBOC) group, the unprotected calixresorcinarene may be reacted with eight equivalents of di-t-butyl dicarbonate.

As noted above, the resist compositions herein additionally include a radiation-sensitive acid generator and a polymeric component.

Upon exposure to radiation, the radiation-sensitive acid generator generates an acid. A variety of photosensitive acid generators (also referred to herein as "PAGs") can be used in the composition of the present invention. Generally, suitable acid generators have a high thermal stability (preferably to temperatures greater than 140° C.) so they are not degraded during pre-exposure processing. Suitable acid generators include ionic iodonium sulfonates, e.g., diaryl iodonium (alkyl or aryl) sulfonate and bis-(di-t-butylphenyl) iodonium camphanylsulfonate; aryl (e.g., phenyl or benzyl) triflates and derivatives and analogs thereof, e.g., triphenylsulfonium triflate or bis-(t-butyl phenyl)iodonium triflate; pyrogallol derivatives (e.g., trimesylate of pyrogallol); onium salts such as triarylsulfonium and diaryliodonium hexafluoroantimonates, hexafluoroarsenates, trifluoromethane sulfonates and others; trifluoromethanesulfonate esters of hydroxyimides, $\alpha,\alpha'$-bis-sulfonyl-diazomethanes; sulfonate esters of nitro-substituted benzyl alcohols; naphthoquinone4-diazides; and alkyl disulfones. Other suitable photoacid generators are disclosed in Reichmanis et al. (1991), *Chemistry of Materials* 3:395, and in U.S. Pat. No. 5,679,495 to Yamachika et al., referenced above. Additional suitable acid generators useful in conjunction with the compositions and methods of the invention will be known to those skilled in the art and/or described in the pertinent literature.

The polymeric component of the resist composition may be in either one of two types: (1) polymers that are inert with respect to the exposure and development process, e.g., are acid-stable; and (2) polymers that exist in a first state prior to exposure to radiation and in a second state following exposure to radiation, wherein the solubility characteristics of the polymer in the first state differ markedly from the solubility characteristics of the polymer in the second state, with regard to the developer solvent ultimately used to provide the resist image. The dissolution inhibitors herein enhance the differential in solubility characteristics of type (2) polymers, insofar as the calix[4]resorcinarenes discussed above provide greater inhibition of dissolution when desired, i.e., in non-acidic conditions. However, the inhibitors quickly dissolve and facilitate dissolution of either type of polymeric component of the resist after contact with the photogenerated acid, when exposed to a basic developer solvent.

With respect to type (1) polymers, such materials are well known in the art and are of course commercially available. Inert polymers include, for example, novolac resins. Novolac resins are the thermoplastic condensation products of a phenol and an aldehyde. Examples of suitable phenols for condensation with an aldehyde, particularly, although not necessarily, formaldehyde, are phenol, m-cresol, o-cresol, p-cresol, 2,4-xylenol, 2,5-xylenol, 3,4-xylenol, 3,5-xylenol and thymol. Preferred novolac resins for use herein are the cresol formaldehyde condensation products. Other inert polymers include, for example, homopolymers or copolymers of vinylphenols.

With regard to a polymer of type (2), the polymer in its "first" state bears acid-cleavable protecting groups that remain intact unless exposed to acid. The acid-cleavable protecting groups are as described above with regard to the dissolution inhibitor. Upon contact with acid, particularly the photogenerated acid, the acid-labile functionalities are cleaved to generate free hydroxyl or carboxylic acid groups, and the polymer is then in its "second" state. Typically, as will be appreciated by those skilled in the art, such polymers generally contain phenolic monomers, which, in the first, protected state, may be, for example, phenyl carbonate esters such as a tBOC-protected phenol or the like. Polymers with ester functionalities that undergo acidolysis are also useful herein, e.g., poly(4-vinylbenzoate)s, polymethacrylates, and the like.

Still other polymers, in fact the preferred polymers herein, are copolymers. Suitable copolymers include, but are not limited to, copolymers comprising a combination of two or more of the following: phenolic monomer units, i.e., substituted or unsubstituted vinylphenols; acrylate monomer units, e.g., substituted or unsubstituted acrylic acid, methacrylic acid, or the like; and styrene monomer units, typically substituted or unsubstituted hydroxystyrene. If substituents are present on any of the foregoing, they must not interfere with the lithographic utility of the polymer. Suitable substituents thus include the halogens, lower alkyl such as methyl or ethyl, and lower alkoxy such as methoxy or ethoxy. Specific and preferred examples of suitable copolymers are as follows: an alternating copolymer of $\alpha,\alpha$-dimethylbenzyl methacrylate with $\alpha$-methylstyrene; a block copolymer of benzyl methacrylate with tetrahydropyranyl methacrylate; and a terpolymer of either of the foregoing with 4-acetoxystyrene. Other suitabler polymers will be known to those skilled in the art or described in the pertinent literature. See, e.g., Ito, "Functional Polymers for Microlithography: Chemically Amplified Imaging Systems," in the *ACS Desk Reference of Functional Polymers* (1997).

The photoresist composition herein preferably comprises approximately 0.5–10 wt. % of the acid generator, up to about 94.5 wt. % polymer, and on the order of 1 wt. % to 40 wt. % dissolution inhibitor. Other customary additives may also be present, including pigments, sensitizers, preservatives, acid-diffusion controlling agents, adhesion promoters, coating aids such as surfactants or anti-foaming agents, adhesion promoters and plasticizers.

Pigments may be used to adjust the optical density of the formulated resist and sensitizer which enhance the activity of photoacid generators by absorbing radiation and transferring it to the photoacid generator. Examples include aromatics such as functionalized benzenes, pyridines, pyrimidines, biphenylenes, indenes, naphthalenes, coumarins, anthraquinones, and other aromatic ketones.

A wide variety of compounds with varying basicity may be used as preservatives and acid-diffusion controlling additives. They may include nitrogenous compounds such as aliphatic primary, secondary, and tertiary amines, cyclic amines such as piperidines, pyrimidines, morpholines, aromatic heterocycles such as pyridines, pyrimidines, purines, imines such as diazabicycloundecene (DBU), guanidines, imides, amides, and others. Ammonium salts of basic anions may also be used, including ammonium, primary, secondary, tertiary, and quaternary alkyl- and arylammonium salts of alkoxides including hydroxide, phenolates, carboxylates, aryl and alkyl sulfonates, sulfonamides, and others. Other cationic nitrogenous compounds including pyridinium salts and salts of other heterocyclic nitrogenous compounds with anions such as alkoxides including hydroxide, phenolates, carboxylates, aryl and alkyl sulfonates, sulfonamides, and the like may also be employed. Surfactants may be used to improve coating uniformity, and include a wide variety of ionic and non-ionic, monomeric, oligomeric, and polymeric species. Likewise, a wide variety of anti-foaming agents may be employed to suppress coating defects. Adhesion promoters may be used as well; again, a wide variety of compounds may be employed to serve this function. A wide variety of monomeric, oligomeric, and polymeric plasticizers such as oligo- and polyethyleneglycol ethers, cycloaliphatic esters, and non-acid reactive steroidally derived materials may be used as plasticizers, if desired. However, neither the classes of compounds nor the specific compounds mentioned above are intended to be comprehensive and/or limiting. One versed in the art will recognize the wide spectrum of commercially available products that may be used to carry out the types of functions that these customary additives perform.

Typically, the sum of all customary additives will comprise less than 20 percent of the solids included in the resist formulation, preferably, less than 5 percent.

The remainder of the resist composition is composed of a solvent. The choice of solvent is governed by many factors not limited to the solubility and miscibility of resist components, the coating process, and safety and environmental regulations. Additionally, inertness to other resist components is desirable. It is also desirable that the solvent possess the appropriate volatility to allow uniform coating of films yet also allow significant reduction or complete removal of residual solvent during the post-application bake process. See, e.g., *Introduction to Microlithography*, Eds. Thompson et al., cited previously. Solvents may generally be chosen from ether-, ester-, hydroxyl-, and ketone-containing compounds, or mixtures of these compounds. Examples of appropriate solvents include cyclopentanone, cyclohexanone, lactate esters such as ethyl lactate, alkylene glycol alkyl ether esters such as propylene glycol methyl ether acetate, alkylene glycol monoalkyl esters such as methyl cellosolve, butyl acetate, 2-ethoxyethanol, and ethyl 3-ethoxypropionate. Preferred solvents include ethyl lactate, propylene glycol methyl ether acetate, and mixtures of ethyl lactate and ethyl 3-ethoxyproprionate. The above list of solvents is for illustrative purposes only and should not be viewed as being comprehensive nor should the choice of solvent be viewed as limiting the invention in any way. Those skilled in the art will recognize that any number of solvents or solvent mixtures may be used.

Greater than 50 percent of the total mass of the resist formulation is typically composed of the solvent, preferably greater than 80 percent. An example of a suitable resist composition is as follows:

| Component | wt. % solids | wt. % total |
|---|---|---|
| Polymer | 50–99 | 5–50 |
| | 80–90 preferred | 10–20 preferred |
| Dissolution Inhibitor (DI) | 1–40 | 0.5–5 |
| Acid Generator | 0.5–10 | 0.05–2 |
| | 1–5 preferred | 0.1–1 |
| Solvent(s) | NA | 50–95 |
| | | 80–90 preferred |
| Other components | 0–20 | 0–4 |
| | 0.001–5 preferred | 0–1 |

The present invention also relates to a process for generating a resist image on a substrate comprising the steps of: (a) coating a substrate with a film comprising the resist composition of the invention; (b) imagewise exposing the film to radiation; and (c) developing the image. The first step involves coating the substrate with a film comprising the resist composition dissolved in a suitable solvent. Suitable substrates are silicon-containing, and include, for example, silicon dioxide, silicon nitride, and silicon oxynitride. The substrate may or may not be coated with an organic anti-reflective layer prior to deposition of the resist composition. Preferably, the surface of the substrate is cleaned by standard procedures before the film is deposited thereon. Suitable solvents for the composition are as described in the preceding section, and include, for example, cyclohexanone, ethyl lactate, and propylene glycol methyl ether acetate. The film can be coated on the substrate using art-known techniques such as spin or spray coating, or doctor blading. Preferably, before the film has been exposed to radiation, the film is heated to an elevated temperature of about 90–150° C. for a short period of time, typically on the order of about 1 minute. The dried film has a thickness of about 0.2–5.0 microns, preferably about 0.3–1.2 microns. In the second step of the process, the film is imagewise exposed to x-ray, electron beam, or ultraviolet radiation, preferably ultraviolet radiation at a wavelength of less than about 300 nm, most preferably radiation having a wavelength of 248 nm. The preferred radiation source in the latter case is a KrF excimer laser. Conveniently, due to the enhanced radiation sensitivity of the resist film, a resist film (1 micron thickness) is fully exposed with less than about 35 mJ/cm$^2$ of radiation, more preferably less than about 25 mJ/cm$^2$. The radiation is absorbed by the radiation-sensitive acid generator to generate free acid which with heating causes cleavage of the acid-cleavable ester substituent and formation of the corresponding acid. Preferably, after the film has been exposed to radiation, the film is again heated to an elevated temperature of about 90–150° C. for a short period of time, on the order of about 1 minute.

The third step involves development of the image with a suitable solvent. Suitable solvents include an aqueous base, preferably an aqueous base without metal ions such as the industry standard developer tetramethyl ammonium hydroxide or choline. The resist composition of the invention has high radiation sensitivity and provides positive images with high contrast and straight walls. The composition can also be readily developed in industry standard developer. Development is without unacceptable thinning or swelling. The resist has suitable thermal properties $T_g$ and good adhesion and planarization. The solubility characteristics of the composition of the present invention can be varied by simply varying the composition of the polymer and/or the degree of protection of the dissolution inhibitor. Because the polymer has a very low optical density in the deep UV, the resist composition is uniquely suitable for use in the deep UV, especially at 248 nm. However, as explained elsewhere herein, the resist composition is also suitable for use in conjunction with processes involving x-ray and electron beam radiation, and, in particular, for improving the contrast obtained using a phase shift mask or x-ray processing.

The composition of the present invention may be used to make an integrated circuit assembly, such as an integrated circuit chip, multichip module, or circuit board. The integrated circuit assembly comprises a circuit formed on a substrate by the steps of (a) coating a substrate with a film comprising the resist composition of the present invention, (b) imagewise exposing the film to radiation, (c) developing the image to expose the substrate, and (d) forming the circuit in the developed film on the substrate by art-known techniques. After the substrate has been exposed, circuit patterns can be formed in the exposed areas by coating the substrate with a conductive material such as conductive metals by art-known dry techniques such as evaporation, sputtering, plating, chemical vapor deposition, or laser-induced deposition. The surface of the film can be milled to remove any excess conductive material. Dielectric materials may also be deposited by similar means during the process of making circuits. Inorganic ions such as boron, phosphorous, or arsenic can be implanted in the substrate in the process for making p-doped or n-doped circuit transistors. Other means for forming circuits are well known to those skilled in the art.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL:

The following examples are put forth so as to provide those of ordinary skill in the art with a complete disclosure and description of how to prepare and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Additionally, all starting materials were obtained commercially or synthesized using known procedures.

Examples 1 through 7 are directed to the preparation of calix[4]resorcinarene precursors used to prepare the functionalized calix[4]resorcinarenes of Examples 8 through 19. Accordingly, Examples 8 through 19 are directed to the synthesis of twelve different calix[4]resorcinarenes bearing acid-labile protecting groups. Example 20 describes the protocol used to assess dissolution inhibition of the various protected calix[4]resorcinarenes synthesized in Examples 8 through 19, along with the results obtained, while Example 21 describes the evaluation of dissolution contrast obtained using a lithographic photoresist composition of the invention.

EXAMPLE 1

Synthesis of C-Tetramethyl-calix[4]resorcinarene Precursor (ccc Isomer)

A solution of 33.03 g (0.3 mol) of resorcinol (obtained from the Aldrich Chemical Co., St. Louis Mo.) and 13.23 mL (0.3 mol) of acetaldehyde in 300 mL of a 50 vol % aqueous ethanol solution was heated to 75° C. To the solution was added dropwise 75 mL of concentrated hydrochloric acid. The reaction mixture was stirred at 75° C. for 1 hr, at which point the mixture was cooled with an ice bath, and a precipitate was collected with a glass filter and dried under reduced pressure. A filtrate was evaporated, and the second precipitate was filtered. The collected precipitate was recrystallized from a 50 vol % aqueous ethanol solution to yield 23.21 g (57%) of a ccc ($C_{4V}$) isomer. The identity of the product was confirmed by $^1$H NMR, $^{13}$C NMR, and IR spectroscopy.

EXAMPLE 2

Synthesis of C-Tetramethyl-calix[4]resorcinarene Precursor (Isomeric Mixture)

To a solution of 33.03 g (0.3 mol) of resorcinol and 13.23 g (0.3 mol) of acetaldehyde in 120 mL of water was added 5 mL of concentrated hydrochloric acid diluted with 5 mL of $H_2O$ over a 15 min period. The reaction mixture was heated at 75° C. for 3 hr and a precipitate was collected with a glass filter every hour. Then the collected precipitate was recrystallized from methanol/water to give 16.46 g (40%) of a ccc isomer. After the recrystallization, the solution was concentrated by rotary evaporation and a residue was recrystallized from acetonitrile to give 1.34 g (3%) of a ctt ($C_{2V}$) isomer. The identity of the product was confirmed by $^1$H NMR, $^{13}$C NMR, and IR spectroscopy.

EXAMPLE 3

Synthesis of C-Tetramethyl-calix[4]resorcinarene Precursors via the Corresponding Acetates A solution of 11.01 g (0.1 mol) of resorcinol and 4.41 mL (0.1 mol) of acetaldehyde in 300 mL of a 50 vol % aqueous ethanol solution was heated to 75° C. To the solution was slowly added 75 mL of concentrated hydrochloric acid. The reaction mixture was stirred for 1 hr, at which point the precipitate formed during the reaction was collected, washed with water, and dried under reduced pressure, to give 13.63 g (100%) of a crude calixarene. The crude calixarene (12.30 g, 22.6 mmol) and a few drops of pyridine were added to 60 mL of acetic anhydride and the solution was stirred at room temperature for 30 min. Excess acetic anhydride was evaporated and 20 mL of methanol was added to the residue. A precipitate was collected with a glass filter and washed with methanol. The obtained powder-like product was recrystallized from acetonitrile to give 0.712 g of a "ctt" isomer as the first fraction and 9.735 g of a "ccc" isomer as the second fraction.

A solution of 4 g of KOH in 50 mL of ethanol was added to a solution of 3.524 g (4 mmol) of ccc calixarene acetate in 50 mL of ethanol. After the reaction mixture was stirred at 60° C. for 30 min, the solution was neutralized with 4 mL of acetic acid. A precipitate was collected with a glass filter and washed with water. The product was recrystallized from a 50 vol % aqueous ethanol solution to yield 1.645 g of ccc calix[4]resorcinarene.

A solution of 0.617 g (0.7 mmol) of ctt calixarene acetate and 0.6 g of KOH in 8 mL of ethanol was stirred at 60° C. for 30 min. The solution was then neutralized with 0.6 mL of acetic acid. A precipitate was collected, washed with water, and recrystallized from a 50 vol % aqueous ethanol solution to yield 0.145 g of ctt calix[4]resorcinarene. The identity of the product was confirmed by $^1$H NMR, $^{13}$C NMR, and IR spectroscopy.

EXAMPLE 4

Synthesis of C-Tetra4-isopropylphenyl-calix[4] resorcinarene Precursor (ctt)

A solution of 8.80 g (0.08 mol) of resorcinol and 11.84 g (0.08 mol) of 4-isopropylbenzaldehyde in 64 mL of ethanol was heated to 75° C. under nitrogen. To the solution was immediately added 1.4 mL of concentrated hydrochloric acid, and the reaction mixture was then stirred at 75° C. for 15 hr. A precipitate formed during the reaction was collected with a glass filter after the reaction mixture was cooled down with an ice-bath. The collected precipitate was washed in 50 mL of refluxing methanol, filtered, and dried under reduced pressure to yield 15.42 g (80%) of a ctt conformer. The identity of the product was confirmed by $^1$H NMR, $^{13}$C NMR, and IR spectroscopy.

EXAMPLE 5

Synthesis of C-Tetra-4-isopropylphenyl-calix[4] resorcinarene Precursor (Mixture of ccc and ctt Isomers)

A solution of 22.02 g (0.2 mol) of resorcinol and 29.64 g (0.2 mol) of 4-isopropylbenzaldehyde in 160 mL of a 50 vol % aqueous ethanol solution was heated at 75° C. under nitrogen. To the solution was immediately added 3.3 mL of concentrated hydrochloric acid, and the reaction mixture was then stirred at 75° C. for 7 hr. A precipitate formed during the reaction was collected with a glass filter after the reaction mixture was cooled down with an ice bath. The precipitate was washed in 70 mL of refluxing methanol for 30 min, separated with a glass filter, and dried under reduced pressure (ctt). The filtrate was placed in a refrigerator overnight and a mixture of isomers was given as a crystal.

Recrystallization from acetonitrile gave 5.88 g of a "ccc" isomer. The identity of the product was confirmed by $^1$H NMR, $^{13}$C NMR, and IR spectroscopy.

EXAMPLE 6

Synthesis of C-Tetraphenyl-calix[4]resorcinarene Precursor (ccc)

A solution of 2.76 g (0.025 mol) of resorcinol and 2.65 g (2.55 mL, 0.025 mol) of benzaldehyde in 20 mL of ethanol was heated at 75° C. under nitrogen. To the solution was immediately added 2.1 mL (0.025 mol) of concentrated hydrochloric acid, and the reaction mixture was then stirred at 75° C. for 20 hr. The mixture containing a yellow precipitate formed during the reaction was poured into 250 mL of a 50 vol % aqueous methanol solution to remove acid. The precipitate was collected with a glass filter and dried under reduced pressure to give 4.637 g (94%) of a crude product. The identity of the product was confirmed by $^1$H NMR, $^{13}$C NMR, and IR spectroscopy.

EXAMPLE 7

Synthesis of C-Tetraphenyl-calix[4]resorcinarene Precursor (ccc-ctt Mixture)

A solution of 2.76 g (0.025 mol) of resorcinol and 2.65 g (2.55 mL, 0.025 mol) of benzaldehyde in 20 mL of a 50 vol % aqueous methanol solution was heated at 75° C. under nitrogen. To the solution was slowly added 2.1 mL (0.025 mol) of concentrated hydrochloric acid, and the reaction mixture was then stirred at 75° C. for several days. The reaction mixture was poured into 250 mL of a 50 vol % aqueous methanol solution to remove acid. The precipitate was collected with a glass filter and dried under reduced pressure. The ctt isomer was isolated by recrystallization from DMF. The identity of the product was confirmed by $^1$H NMR, $^{13}$C NMR, and IR spectroscopy.

EXAMPLE 8

Synthesis of O-Octa-t-butoxycarbonylmethyl-C-tetramethyl-calix[4]resorcinarene (ccc)

To a solution of 1.63 g (3 mmol) of C-tetramethyl-calix[4]resorcinarene (ccc) in 30 mL of dry acetone were added 4.56 g (33 mmol) of potassium carbonate, 0.70 g (2.64 mmol) of 18-crown-6 and 5.15 g (26.4 mmol) t-butyl bromoacetate. The reaction mixture was refluxed with vigorous stirring. After 72 h, the mixture was poured into 200 mL of water, and then a precipitate was collected with a glass filter, washed with water and methanol, and recrystallized from 2-propanol to give 2.65 g (61%) of ccc O-octa-tBOC-C-tetramethy-calix[4]resorcinarene. The identity of the product was confirmed by $^1$H NMR, $^{13}$C NMR, and IR spectroscopy.

EXAMPLE 9

Synthesis of O-Octa-t-butoxycarbonylmethyl-C-tetramethyl-calix[4]resorcinarene (ctt)

Sodium hydride (0.576 g, 60 wt % in oil) was dispersed in a solvent mixture of DMF and THF (2.5 mL/7 mL). To the mixture was added in a 30 min period a suspension of 0.817 g (1.5 mmol) of C-tetramethyl-calix[4]resorcinarene (ctt) and 2.808 g (14.4 mmol) of t-butyl bromoacetate in a mixture of DMF and THF (2.5 mL/1 mL), and then the reaction mixture was vigorously stirred for 12 h. An insoluble part was filtered off and a filtrate was evaporated. The white solid thus obtained was washed with water and methanol, and recrystallized from toluene/cyclohexane to give 1.266 g (58%) of the ester. The identity of the product was confirmed by $^1$H NMR, $^{13}$C NMR, and IR spectroscopy.

EXAMPLE 10

Synthesis of O-Octa-t-butoxycarbonyl (tBOC)-C-tetramethyl-calix[4]resorcinarene (ccc)

Pyridine (0.08 mL) was added to a solution of 6.76 g (1.5 mmol) of C-tetramethyl-calix[4]resorcinarene (ccc) and 2.881 g (13.2 mmol) of di-t-butyl dicarbonate in 20 mL of dry acetone. The reaction mixture was refluxed for 15 hr and concentrated by rotary evaporation to give a yellow solid. Recrystallization from acetone yielded 1.910 g (95%) of ccc O-octa-tBOC-C-tetramethyl-calix[4]resorcinarene. The identity of the product was confirmed by $^1$H NMR, $^{13}$C NMR, and IR spectroscopy.

EXAMPLE 11

Synthesis of O-Octa-tBOC-C-tetramethyl-calix[4] resorcinarene (ctt)

One drop of pyridine was added to a solution of 0.817 g (1.5 mmol) of C-tetramethyl-calix[4]resorcinarene (ctt) and 2.881 g (13.2 mmol) of di-t-butyl dicarbonate in 20 mL of dry acetone. The reaction mixture was refluxed for 15 h and concentrated by rotary evaporation to give a yellow solid. Recrystallization from acetone provided 1.910 g (95%) of ctt O-octa-tBOC-C-tetramethyl-calix[4]resorcinarene. The identity of the product was confirmed by $^1$H NMR, 13C NMR, and IR spectroscopy.

EXAMPLE 12

Synthesis of O-Octa-t-butoxycarbonylmethyl-C-tetra-4-isopropylphenyl-calix[4]resorcinarene(ccc)

To a solution of 2.88 g (3 mmol) of C-tetra-4-isopropylpheny-calix[4]resorcinarene (ccc) in 30 mL of dry acetone were added 6.63 g (48 mmol) of potassium carbonate, 0.63 g (2.4 mmol) of 18-crown-6, and 6.63 g (26.4 mmol) of t-butyl bromoacetate. The reaction mixture was refluxed with vigorous stirring. After 72 h, the mixture was poured into 200 mL of water. Then a precipitate was collected with a glass filter, washed with water and methanol, and recrystallized from 2-propanol to give 4.16 g (74%) of ccc O-octa-t-butoxycarbonylmethyl-C-tetra-4-isopropylphenyl-calix[4]resorcinarene. The identity of the product was confirmed by $^1$H NMR, $^{13}$C NMR, and IR spectroscopy.

EXAMPLE 13

Synthesis of O-Octa-t-butoxycarbonylmethyl-C-tetra-4-isopropylphenyl-calix[4]resorcinarene (ctt)

To a solution of 9.61 g (0.01 mol) of C-tetra-4-isopropylphenyl-calix[4]resorcinarene (ctt) in 100 mL of dry acetone were added 22.11 g (0.16 mol) of potassium carbonate, 2.1 g (0.008 mol) of 18-crown-6, and 17.17 g (0.088 mmol) of t-butyl bromoacetate. The reaction mixture was refluxed with vigorous stirring. After 72 h, the mixture was poured into 500 mL of water. Then a precipitate was collected with a glass filter, washed with water and methanol, and recrystallized from 2-propanol to give 10.49 g (56%) of ctt O-octa-t-butoxycarbonylmethyl-C-tetra-4- isopropylphenyl-calix[4]resorcinarene. The identity of the product was confirmed by $^1$H NMR, $^{13}$C NMR, and IR spectroscopy.

EXAMPLE 14

Synthesis of O-Octa-tBOC-C-tetra-4-isopropylphenyl-calix[4]resorcinarene (ccc)

One drop of pyridine was added to a solution of 2.884 g (3 mmol) of C-tetra-4-isopropylphenyl-calix[4]resorcinarene (ccc) and 5.763 g (26.4 mmol) of di-t-butyl dicarbonate in 30 mL of dry acetone, and then the reaction solution was refluxed. After 20 h, the solvent was evaporated and a residue was recrystallized from 2-propanol to give 4.303 g (81%) of O-octa-tBOC-C-tetra-4-isopropylphenyl-calix[4]resorcinarene (ccc). The identity of the product was confirmed by $^1$H NMR, $^{13}$C NMR, and IR spectroscopy.

EXAMPLE 15

Synthesis of O-Octa-tBOC-C-tetra-4-isopropylphenyl-calix[4]resorcinarene (ctt)

One drop of pyridine was added to a solution of 1.752 g (1.82 mmol) of C-tetra-4-isopropylphenyl-calix[4]resorcinarene (ctt) and 3.501 g (26.4 mmol) of di-t-butyl dicarbonate in 20 mL of dry acetone, and then the solution was refluxed. After 20 h, the solvent was evaporated and a residue recrystallized from a mixed solvent of cyclohexane and toluene to give 2.193 g (68%) of O-octa-tBOC-C-tetra-4-isopropylphenyl-calix[4]resorcinarene (ctt). The identity of the product was confirmed by $^1$H NMR, $^{13}$C NMR, and IR spectroscopy.

EXAMPLE 16

Synthesis of O-Octa-t-butoxycarbonylmethyl-C-tetraphenyl-calix[4]resorcinarene (ccc)

To a suspension of 1.586 g (2 mmol) of C-tetraphenyl-calix[4]resorcinarene (ccc) in 20 mL of dry acetone were added 4.423 g (32 mmol) of potassium carbonate, 0.423 g (1.6 mmol) of 18-crown-6, and 3.504 g (17.6 mmol) of t-butyl bromoacetate. The reaction mixture was refluxed with vigorous stirring. After 72 h, the mixture was poured into 150 mL of water. Then a precipitate was collected with a glass filter, washed with water and methanol, and recrystallized from 2-propanol/acetone to give 2.290 g (67%) of O-octa-t-butoxycarbonylmethyl-C-tetraphenyl-calix[4]resorcinarene (ccc). The identity of the product was confirmed by $^1$H NMR, $^{13}$C NMR, and IR spectroscopy.

EXAMPLE 17

Synthesis of O-Octa-t-butoxycarbonylmethyl-C-tetraphenyl-calix[4]resorcinarene (ctt)

To a suspension of 1.586 g (2 mmol) of C-tetraphenyl-calix[4]resorcinarene (ctt) in 20 mL of dry acetone were added 4.423 g (32 mmol) of potassium carbonate, 0.423 g (1.6 mmol) of 18-crown-6, and 3.504 g (17.6 mmol) of t-butyl bromoacetate. The reaction mixture was refluxed with vigorous stirring. After 72 h, the mixture was poured into 150 mL of water. A precipitate was then collected with a glass filter, washed with water and methanol, and recrystallized from acetone to give 2.500 g (73%) of O-octa-t-butoxycarbonylmethyl-C-tetraphenyl-calix[4]resorcinarene (ctt). The identity of the product was confirmed by $^1$H NMR, $^{13}$C NMR, and IR spectroscopy.

EXAMPLE 18

Synthesis of O-Octa-tBOC-C-tetraphenyl-calix[4]resorcinarene (ccc)

One drop of pyridine was added to a suspension of 1.586 g (2 mmol) of C-tetraphenyl-calix[4]resorcinarene (ccc) and 3.841 g (17.6 mmol) of di-t-butyl dicarbonate in 30 mL of dry acetone, and then the reaction mixture was refluxed. An insoluble part completely disappeared. The reaction was continued for 20 h and then the solvent evaporated. A residue was subjected to recrystallization from acetone/2-propanol to give 1.153 g (40%) of O-octa-tBOC-C-tetraphenyl-calix[4]resorcinarene (ccc). The identity of the product was confirmed by $^1$H NMR, $^{13}$C NMR, and IR spectroscopy.

EXAMPLE 19

Synthesis of O-Octa-tBOC-C-tetraphenyl-calix[4]resorcinarene (ctt)

One drop of pyridine was added to a suspension of 1.586 g (2 mmol) of C-tetraphenyl-calix[4]resorcinarene (ctt) and 3.841 g (17.6 mmol) of di-t-butyl dicarbonate in 30 mL of dry acetone, and the reaction mixture was then refluxed for 20 h. In this case, an insoluble part still remained after 20 h. A residue obtained after evaporation of the solvent was recrystallized from acetone to give 1.463 g (46%) of O-octa-tBOC-C-tetraphenyl-calix[4]resorcinarene (ctt). The identity of the product was confirmed by $^1$H NMR, $^{13}$C NMR, and IR spectroscopy.

EXAMPLE 20

Evaluation of Dissolution Inhibition

The calixarene ester or carbonate was added to a solution of a copolymer of t-butyl acrylate, or "TBA," with 4-hydroxystyrene, or "HOST," dissolved in propylene glycol methyl ether acetate (PGMEA) at a loading varying from 5 to 25 wt %. The copolymer employed in this study had a composition of HOST/TBA=70/30. Spin-cast films were baked at 120° C. for 60 sec. The dissolution kinetics of the films containing the protected calixarenes were studied using a quartz crystal microbalance (QCM) in a 0.26 N tetramethylammonium hydroxide (TMAH) aqueous solution (CD-26).

Figure 1:
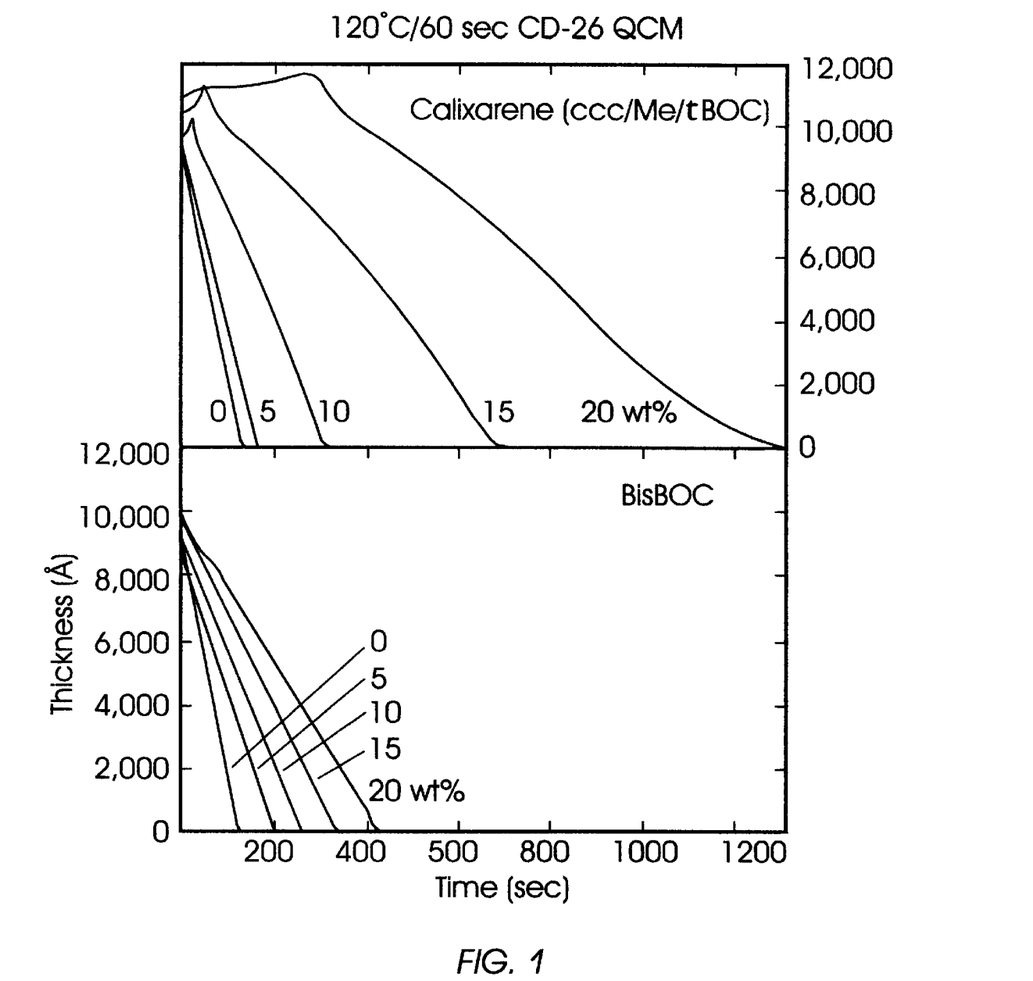
FIG. 1 is a graph illustrating the difference in dissolution kinetics between compositions containing a dissolution inhibitor of the invention and analogous compositions containing a known dissolution inhibitor, BisBOC (as described in Example 20).
Figure 2:
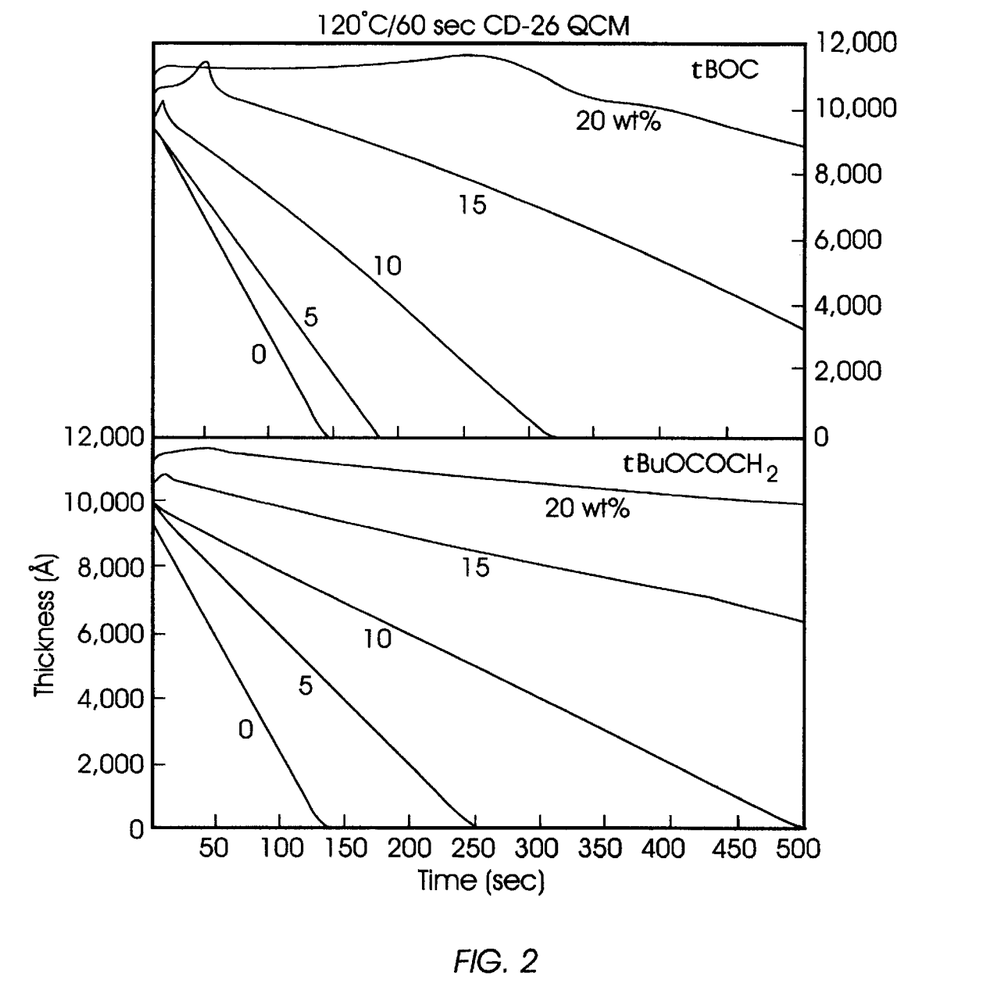
FIG. 2 is a graph illustrating the difference in dissolution kinetics between compositions containing two different dissolution inhibitors of the invention (as described in Example 20).

All the twelve derivatives prepared with different isomeric structures, substituents, and acid-labile protecting groups were subjected to the dissolution behavior investigation. Two sets of the dissolution kinetics curves are presented in FIGS. 1 and 2. It is clear that the protected ccc methyl-calixarene exhibits a much stronger inhibition effect than BisBOC and that the calixarene system provides an induction period, as long as 5 min at 20 wt % loading (FIG. 1). In FIG. 2 are compared the t-butyl ester protection group with tBOC using the ccc isomer of methyl-calixarene. While the tBOC group tends to show a longer induction period, the t-butyl ester functionality is more effective in reducing the dissolution rate at the same weight or mole % loading.

Figure 3:
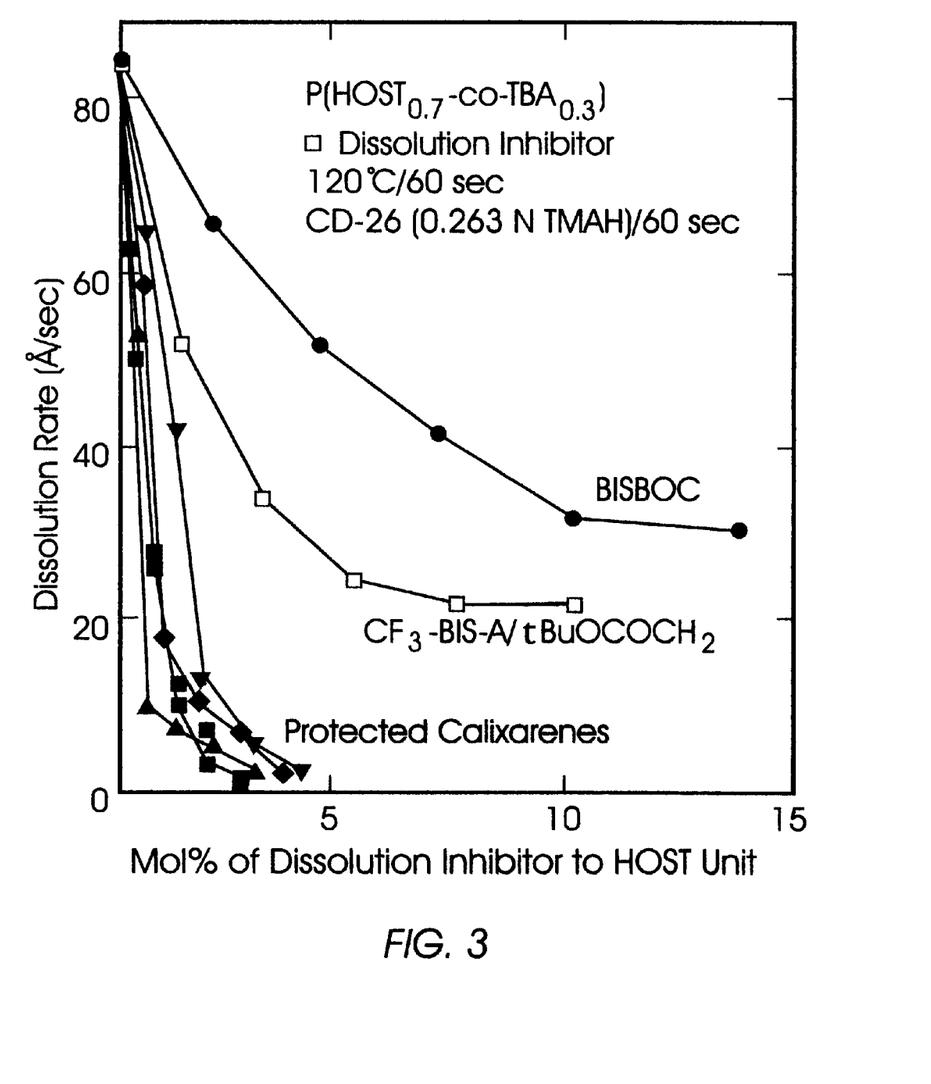
FIG. 3 is a graph illustrating the effect of dissolution inhibitor "loading" on dissolution rate, for a composition of the invention and for compositions containing known dissolution inhibitors, BisBOC and $CF_3$-Bis-A/tBuOCOCH$_3$ (6F-Bisphenol A protected with a t-butoxycarbonylmethyl group (again, as described in Example 20).

The calixarene esters and carbonates are bulky and heavy molecules (having molecular weights ranging from 1345 to 1874) and are particularly impressive in their dissolution inhibition capability when compared with smaller difunctional dissolution inhibitors such as BisBOC on the basis of mole %. FIG. 3 presents the effect of loading in mole % of the five protected calixarenes on the dissolution rate of the copolymer in CD-26 in comparison with BisBOC and 6F-Bisphenol A protected with a t-butoxycarbonylmethyl group. All the calixarene derivatives investigated in this study exhibited a similar and strong loading effect, much stronger than the small bifunctional inhibitors. Furthermore, the calixarene derivatives can bring the dissolution rate down to <5% while the maximum dissolution rate reduction achieved with the bifunctional compounds is only 75–65%

EXAMPLE 21

Evaluation of Dissolution Contrast

Figure 4:
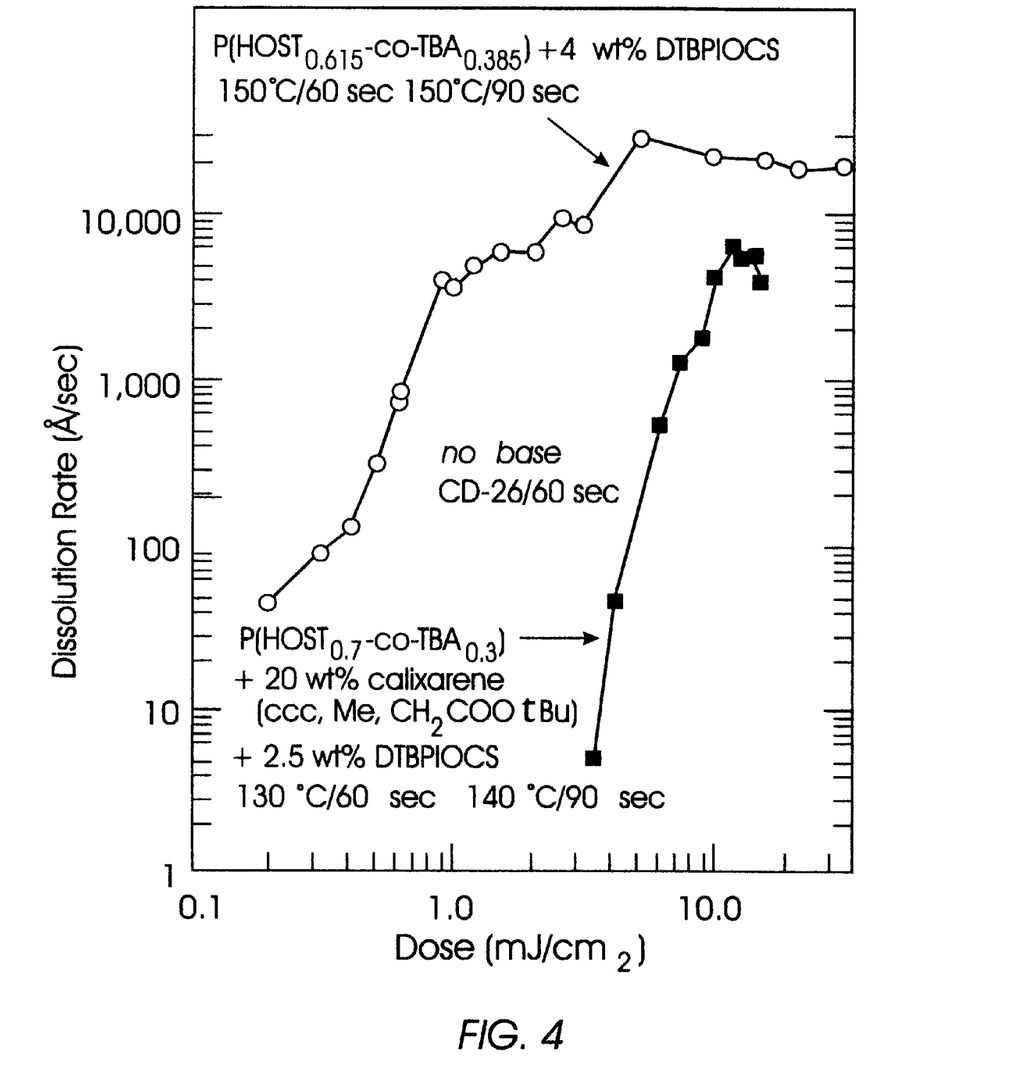
FIG. 4 is a graph illustrating the correlation between dissolution rate and exposure dose for both a lithographic photoresist composition of the invention and a prior composition not containing the dissolution inhibitors disclosed and claimed herein (as described in Example 21).

An ESCAP-type resist was formulated using the copolymer described in the preceding example, with 30 mol % TBA, 20 wt % ccc methyl-calixarene protected with $CH_2COOtBu$, and 2.5 wt % bis-(di-t-butylphenyl)iodonium camphanylsulfonate (DTBPIOCS) in PGMEA. The films were baked at 130° C. for 60 sec, exposed to 254 nm radiation, postexposure-baked at 140° C. for 90 sec, and developed with CD-26. The dissolution rate is plotted as a function of exposure dose in FIG. 4 in comparison with an ESCAP resist composed of a copolymer containing 38% TBA and 4 wt % DTBPIOCS. No base additives were employed. Although the new three-component formulation is less sensitive due to the lower PAG loading and lower postexposure-bake temperature, its developer selectivity is much higher than the two-component reference.

Thus, the calixarene-based dissolution inhibitors can be expected to improve the lithographic performance of chemically amplified positive resists.

What is claimed is:

1. An improved lithographic photoresist composition comprising a radiation-sensitive acid generator, a polymeric component and a dissolution inhibitor, wherein the improvement comprises employing as the dissolution inhibitor a calix[4]resorcinarene partially or wholly protected with acid-labile protecting groups, wherein the calix[4] resorcinarene is in the $C_{2V}$ configuration, the $C_{4V}$ configuration, or is a mixture thereof.

2. The composition of claim 1, wherein the dissolution inhibitor has the structure of formula (I)

(I)

wherein:
the R moieties may be the same or different and are selected from the group consisting of hydrogen and acid-labile protecting groups, with the proviso that at least one of the R moieties is an acid-labile protecting group;
the R' moieties are independently selected from the group consisting of hydrogen, halogen, nitro, alkyl, aryl, and alkaryl, and, if alkyl, aryl or alkaryl, optionally substituted with one to four substituents selected from the group consisting of hydroxy, halogen, lower alkyl, lower alkoxy and nitro; and
the X and Y moieties may be the same or different and are selected from the group consisting of hydrogen, alkyl, alkoxy, aryl, aralkyl, alkaryl, halo, cyano, nitro and carboxylate.

3. The composition of claim 2, wherein:
the R' are independently selected from the group consisting of hydrogen, bromo, $C_1$–$C_{12}$ alkyl, and $C_1$–$C_{12}$ alkyl substituted with a hydroxyl group, a halogen atom, a phenyl ring, or a phenyl ring bearing a hydroxy, halogen or lower alkyl substituent.

4. The composition of claim 3, wherein:
all X moieties are hydrogen, and the Y moieties are selected from the group consisting of hydrogen and lower alkyl.

5. The composition of claim 2, wherein:
all X moieties are hydrogen, and the Y moieties are selected from the group consisting of hydrogen and lower alkyl.

6. The composition of 2, wherein the acid-labile protecting groups have the structural formula in which m is 0 or 1 and $R^1$ is $CR^2R^3R^4$ wherein $R^2$, $R^3$ and $R^4$ are independently hydrogen, alkyl or aryl.

7. The composition of claim 1, wherein at least half of the free hydroxyl groups of the calix[4]resorcinarene are protected with acid-labile protecting groups.

8. The composition of claim 1, wherein the calix[4] resorcinarene is in the $C_{2V}$ configuration.

9. The composition of claim 1, wherein the calix[4] resorcinarene is in the $C_{4V}$ configuration.

10. The composition of claim 1, wherein the dissolution inhibitor comprises a mixture of calix[4]resorcinarene in the $C_{2V}$ configuration and calix[4]resorcinarene in the $C_{4V}$ configuration.

11. A process for generating a resist image on a substrate, comprising the steps of:
(a) coating a substrate with a film comprising the composition of claim 1;
(b) exposing the film selectively to a predetermined pattern of radiation to form a latent image therein; and
(c) developing the latent image with a developer.

12. The process of claim 11, wherein after step (a), and prior to step (b), the film is dried.

13. The process of claim 12, wherein after step (b), and prior to step (c), the film is heated to a temperature in the range of approximately 90° C. to 150° C.

14. The process of claim 11, wherein after step (b), and prior to step (c), the film is heated to a temperature in the range of approximately 90° C. to 150° C.

15. The process of claim 11, wherein the radiation is ultraviolet radiation.

16. The process of claim 15, wherein the radiation has a wavelength of 248 nm.

17. A lithographic photoresist composition, comprising:
(a) a radiation-sensitive acid generator which generates an acid upon exposure to radiation;

(b) a photoresist binder; and
(c) a dissolution inhibitor comprising a calix[4] resorcinarene partially or wholly protected with acid-labile protecting groups, wherein the calix[4] resorcinarene is in the $C_{2V}$ or $C_{4V}$ configuration.

18. The composition of claim 17, wherein the photoresist binder comprises an acid-stable polymer.

19. The composition of claim 18, wherein the acid-stable polymer is a novolac resin.

20. The composition of claim 19, wherein the novolac resin is a thermoplastic condensation product of (a) a phenolic compound selected from the group consisting of phenol, m-cresol, o-cresol, p-cresol, 2,4-xylenol, 2,5-xylenol, 3,4-xylenol, 3,5-xylenol, thymol, and combinations thereof, with (b) an aldehyde.

21. The composition of claim 20, wherein the novolac resin is a thermoplastic condensation product of a cresol and formaldehyde.

22. The composition of claim 18, wherein the acid-stable polymer is a homopolymer or copolymer of a poly(vinylphenol).

23. The composition of claim 17, wherein the photoresist binder comprises a polymer which exists in either an intact, acid-sensitive state or in a post-exposure, acid-cleaved state, wherein, in the intact, acid-sensitive state the polymer is substantially insoluble in polar solvents, while in the post-exposure, acid-cleaved state, the polymer is substantially soluble in polar solvents.

24. The composition of claim 23, wherein the polymer is a copolymer comprising phenolic monomer units and non-phenolic monomer units.

25. The composition of claim 23, wherein the polymer is a copolymer comprising at least two of: phenolic monomer units; acrylate monomer units; and styrene monomer units.

26. The composition of claim 17, wherein the dissolution inhibitor has the structure of formula (I)

(I)

wherein:
the R moieties may be the same or different and are selected from the group consisting of hydrogen and acid-labile protecting groups, with the proviso that at least one of the R moieties is an acid-labile protecting group;
the R' moieties are independently selected from the group consisting of hydrogen, halogen, nitro, alkyl, aryl, and alkaryl, and, if alkyl, aryl or alkaryl, optionally substituted with one to four substituents selected from the group consisting of hydroxy, halogen, lower alkyl, lower alkoxy and nitro; and the X and Y moieties may be the same or different and are selected from the group consisting of hydrogen, alkyl, alkoxy, aryl, aralkyl, alkaryl, halo, cyano, nitro and carboxylate.

27. The composition of claim 26, wherein:
the R' are independently selected from the group consisting of hydrogen, bromo, $C_1$–$C_{12}$ alkyl, and $C_1$–$C_{12}$ alkyl substituted with a hydroxyl group, a halogen atom, a phenyl ring, or a phenyl ring bearing a hydroxy, halogen or lower alkyl substituent.

28. The composition of claim 27, wherein:
all X moieties are hydrogen, and the Y moieties are selected from the group consisting of hydrogen and lower alkyl.

29. The composition of claim 26, wherein:
all X moieties are hydrogen, and the Y moieties are selected from the group consisting of hydrogen and lower alkyl.

30. The composition of 26, wherein the acid-labile protecting groups have the structural formula in which m is 0 or 1 and $R^1$ is $CR^2R^3R^4$ wherein $R^2$, $R^3$ and $R^4$ are independently hydrogen, alkyl or aryl.

31. The composition of claim 17, wherein at least half of the free hydroxyl groups of the calix[4]resorcinarene are protected with acid-labile protecting groups.

32. The composition of claim 17, wherein the calix[4] resorcinarene is in the $C_{2V}$ configuration.

33. The composition of claim 17, wherein the calix[4] resorcinarene is in the $C_{4V}$ configuration.

34. The composition of claim 17, wherein the dissolution inhibitor comprises a mixture of calix[4]resorcinarene in the $C_{2V}$ configuration and calix[4]resorcinarene in the $C_{4V}$ configuration.

35. A process for generating a resist image on a substrate, comprising the steps of:
(a) coating a substrate with a film comprising the composition of claim 17;
(b) exposing the film selectively to a predetermined pattern of radiation to form a latent image therein; and
(c) developing the latent image with a developer.

36. The process of claim 35, wherein after step (a), and prior to step (b), the film is dried.

37. The process of claim 36, wherein after step (b), and prior to step (c), the film is heated to a temperature in the range of approximately 90° C. to 150° C.

38. The process of claim 35, wherein the radiation is x-ray, electron beam, or ultraviolet radiation.

39. The process of claim 35, wherein the radiation is ultraviolet radiation.

40. The process of claim 39, wherein the radiation has a wavelength of 248 nm.

41. A compound having the structure of formula (I)

(I)

wherein:

the R moieties may be the same or different and are selected from the group consisting of hydrogen and acid-labile protecting groups having the structural formula in which m is 0 or 1 and $R^1$ is $CR^2R^3R^4$ wherein $R^2$, $R^3$ and $R^4$ are independently hydrogen, alkyl or aryl, with the proviso that at least one of the R moieties is an acid-labile protecting group;

the R' moieties are independently selected from the group consisting of hydrogen, halogen, nitro, alkyl, aryl, and alkaryl, and, if alkyl, aryl or alkaryl, optionally substituted with one to four substituents selected from the group consisting of hydroxy, halogen, lower alkyl, lower alkoxy and nitro;

the X and Y moieties may be the same or different and are selected from the group consisting of hydrogen, alkyl, alkoxy, aryl, aralkyl, alkaryl, halo, cyano, nitro and carboxylate; and the compound is in the $C_{2V}$ or $C_{4V}$ configuration.

42. The compound of claim 41, wherein:

the R' are independently selected from the group consisting of hydrogen, bromo, $C_1$–$C_{12}$ alkyl, and $C_1$–$C_{12}$ alkyl substituted with a hydroxyl group, a halogen atom, a phenyl ring, or a phenyl ring bearing a hydroxy, halogen or lower alkyl substituent.

43. The compound of claim 42, wherein:

all X moieties are hydrogen, and the Y moieties are selected from the group consisting of hydrogen and lower alkyl.

44. The compound of claim 41, wherein:

all X moieties are hydrogen, and the Y moieties are selected from the group consisting of hydrogen and lower alkyl.

45. The compound of claim 41, in the $C_{2V}$ configuration.

46. The compound of claim 41, in the $C_{4V}$ configuration.

47. The compound of claim 41, comprising a mixture of $C_{2V}$ and $C_{4V}$ isomers.

48. The compound of claim 41, wherein all R' moieties are identical.

49. Calix[4]resorcinarenes that are partially protected with acid-cleavable protecting groups, and are in the $C_{2V}$ configuration or the $C_{4V}$ configuration.

50. Calix[4]resorcinarenes that are partially protected with acid-cleavable ether groups, and are in the $C_{2V}$ configuration or the $C_{4V}$ configuration.

51. A compound having the structure of formula (I)

(I)

wherein:

the R moieties may be the same or different and are selected from the group consisting of hydrogen and acid-labile protecting groups, with the proviso that at least one but not all of the R moieties is an acid-labile protecting group;

the R' moieties are independently selected from the group consisting of hydrogen, halogen, nitro, alkyl, aryl, and alkaryl, and, if alkyl, aryl or alkaryl, optionally substituted with one to four substituents selected from the group consisting of hydroxy, halogen, lower alkyl, lower alkoxy and nitro;

the X and Y moieties may be the same or different and are selected from the group consisting of hydrogen, alkyl, alkoxy, aryl, aralkyl, alkaryl, halo, cyano, nitro and carboxylate; and the compound is in the $C_{2V}$ or $C_{4V}$ configuration.

52. The compound of claim 51, wherein all R' moieties are identical.

* * * * *